United States Patent [19]
Stuhmer et al.

[11] Patent Number: 4,919,677
[45] Date of Patent: Apr. 24, 1990

[54] PROSTHETIC ACETABULUM

[75] Inventors: Karl-Gerhart Stuhmer, Ravensburg, Fed. Rep. of Germany; Rudolf Koch, Berlingen; Otto Frey, Winterthur, both of Switzerland

[73] Assignee: Sulzer Brothers Limited, Winterthur, Switzerland

[21] Appl. No.: 392,709

[22] Filed: Aug. 11, 1989

[30] Foreign Application Priority Data

Aug. 25, 1988 [CH] Switzerland .................. 3168/88

[51] Int. Cl.$^5$ .............................................. A61F 2/32
[52] U.S. Cl. ........................................ 623/22; 623/18
[58] Field of Search ................ 623/22, 23, 18, 16, 623/20

[56] References Cited

U.S. PATENT DOCUMENTS

| | | | |
|---|---|---|---|
| 3,977,026 | 8/1976 | Battault | 623/22 X |
| 4,662,891 | 5/1987 | Noiles | 623/22 |
| 4,715,859 | 12/1987 | Schelhas et al. | 623/22 |
| 4,822,367 | 4/1989 | Stuhmer | 623/22 |

FOREIGN PATENT DOCUMENTS

| | | | |
|---|---|---|---|
| 0058753 | 9/1982 | European Pat. Off. | 623/22 |
| 0237751 | 9/1987 | European Pat. Off. | 623/22 |
| 2184159 | 12/1973 | France | 623/22 |
| 2272637 | 12/1975 | France | 623/22 |

OTHER PUBLICATIONS

M. Ungethum, et al., Biomechanical Aspects of Non-Cemented Prosthetic Hip Sockets, Medizinisch Orthopadische Technik, vol. 106, No. 6, Nov./Dec. 1986, Stuttgart, Germany.

*Primary Examiner*—Ronald L. Frinks
*Attorney, Agent, or Firm*—Kenyon & Kenyon

[57] ABSTRACT

The turns of the self-tapping screwthread formed on the outside surface of the metal hemispherical shell have front portions of constant thickness which extend over one third of the cross sectional length of the thread turn. The remainder of the thread turns is wedge-shaped. The shape of the thread turns facilitates the cutting in of the screw thread when the hemispherical shell is being implanted.

10 Claims, 1 Drawing Sheet

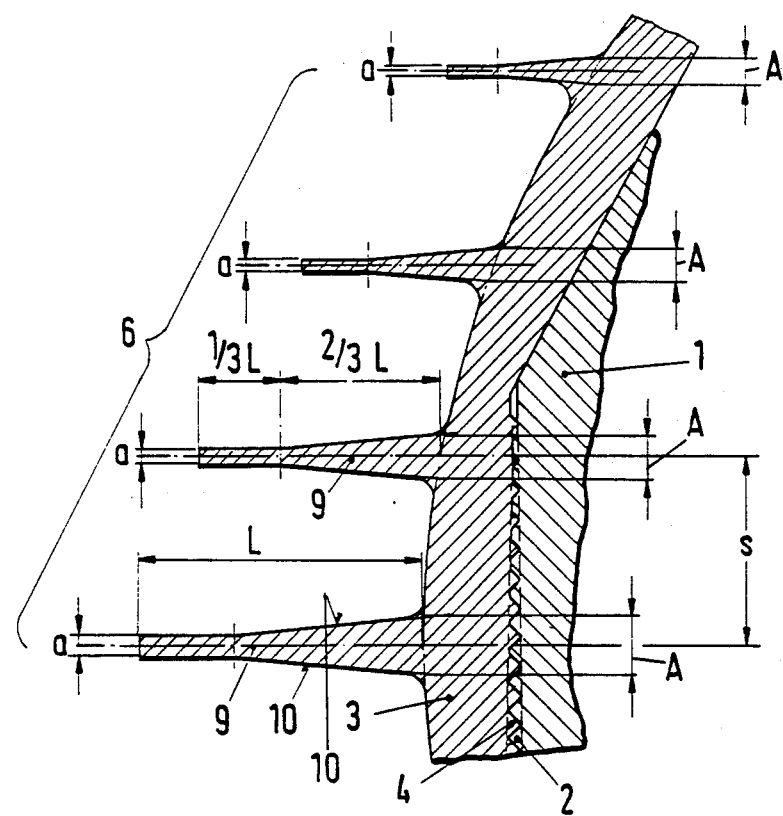

PROSTHETIC ACETABULUM

This invention relates to a prosthetic acetabulum. More particularly, this invention relates to a prosthetic acetabulum for cementless fixation in a pelvis.

Heretofore, various types of prosthetic acetabulue have been known for implanting in a pelvis. In some cases, the acetabulum has been provided with a self-tapping screwthread on an outer surface in order to be threaded into the pelvis during operation. For example, European Patent Application 0237751 describes an acetabulum having a hemispherical outer shell of pure titanium or of a titanium alloy with a constant pitch self-tapping screw threaded on the outside surface having spaced apart teeth. In addition, the thread is of a wedge-shape having a cross-sectional length of from 3 millimeters to 8 millimeters, a root width of from 25% to 70% of the length and a crest width of from 10% to 40% of the length. Generally, if these dimensions are observed, a relatively extensive bone compaction can be produced during threading in of the acetabulum in a bone cavity. This leads to a very stable cementless anchorage of the acetabulum in the bone with outstanding resistance to accidental rotation.

However, it has been found in practice that considerable difficulties confront the operating surgeon where the acetabulum has a wedge-shaped screwthread as above described. This is because the wedge shaped screwthread rapidly seizes up during cutting.

Other types of anchoring structures for acetabula are also known, for example, from European Pat. No. 0058753 and French Pat. Nos. 2,184,159 and 2,272,637. However, these anchoring systems have external ribs of generally rectangular cross-sectional shape for implantation, for example in bone cement beds. Other types of non-cemented screwed sockets have also been known as described by M. Ungethum, et al, Biomechanical Aspects of Non-Cemented Prosthetic Hip Sockets, Medizinisch Orthopadische Technik, Vol. 106, No. 6, November/December 1986, Stuttgart, Germany.

Accordingly, it is an object of the invention to provide an acetabulum with an improved screwthread to facilitate threading into a pelvic bone.

It is another object of the invention to reduce the time required for surgical implantation of an acetabulum having a self-tapping screwthread.

Briefly, the invention provides a prosthetic acetabulum for cementless fixation in a pelvis having a hemispherical outer shell of biocompatible material and a constant-pitch self-tapping screwthread on an outer peripheral surface of the shell. In accordance with the invention, the thread has a cross-sectional shape of constant thickness from a free end over a portion of the cross-sectional length thereof and an increasing thickness towards the peripheral surface of the shell over the remainder of the length. In this respect, the portion of constant thickness extends from the free end of the thread over one-third of the length of the thread.

It has been found that the first third of a thread is particularly effective in facilitating thread-cutting whereas the remaining two-thirds of the thread ensures a firm fit.

These and other objects and advantages of the invention will become more apparent from the following detailed description taken in conjunction with the accompanying drawing wherein:

The drawing illustrates a meridian sectional view through an equatorial zone of an acetabulum having a screwthread in accordance with the invention.

As illustrated, the acetabulum has two parts. A first part is in the form of a cup or socket body 1 having an outer boundary forming a polygon in cross section whose equatorial sides have a screwthread 2. The other part is formed by a one piece metal hemispherical shell of biocompatible material such as a metal selected from the group consisting of titanium and a titanium alloy. The shell 3 is provided with a companion screwthread 4 on the inside to threadably engage with the screwthread 2 of the socket body 1. In this respect, the shell 3 is provided with an internal cavity which is adapted to the outer boundary of the socket body 1. A suitable socket shell (not shown) in the form of a hollow hemisphere may be worked into the socket body 1 in order to receive the head of a prosthetic femoral head (not shown).

As illustrated, the hemispherical shell 3 is provided with a constant-pitch self-tapping screwthread on the outer peripheral surface in order to anchor the shell 3 in a pelvis bone. The screwthread 6 is, in known manner, placed within zones of average "latitudes" and near the equator of the shell with a constant pitch s, for example, of 6.5 millimeters. As is known, the screwthread 6 is in the form of a multistart screwthread.

The turns 9 of the thread 6 are spaced apart and may be subdivided in the peripheral direction by gaps (not shown) each of which extends in the meridian direction of the shell 3. In addition, the length L of the respective turns 9 of the thread 6 decrease continuously from the equator towards the pole in the illustrated embodiment. This length L is measured in the center plane of each thread turn as the distance between the surface of the shell 3 and the crest or free end of the thread turn 9. This cross sectional length is of from 3 millimeters to 8 millimeters where the shell 3 is made of titanium or titanium alloy.

The thickness A, that is the root width or thickness of a thread turn 9 is measured from the corners which are rounded by a fillet-like radius where the prolonged flanks 10 of a thread turn 9 intersects with the surface of the outer shell 3. This root width is from 25% to 70% of the length L of the thread. In addition, the discrete screw turns 9 each have a crest thickness a of from 10% to 40% of the length L of the thread turn 9.

As indicated, each thread turn 9 has a cross sectional shape of constant thickness from the free end over one-third the cross-sectional length L thereof with an increasing thickness towards the surface of the shell 3 over the remaining two-thirds of the length L. That is, the front third of each thread turn has parallel flanks. As such, the front third of each thread turn greatly facilitates the cutting in of the screw thread 6, as compared with previously known threads, since the thread turn 9 cannot jam in the bone in the front-third part.

In producing the screwthread 3, the discrete thread turns 9 may be formed during the production of the shell 3, for example, by numerically controlled thread-cutting or by cutting out from a solid blank.

The invention thus provides a metal hemispherical shell for an acetabulum with a screwthread which facilitates cutting into a pelvic bone during operation. In this respect, the shape of the end portions of the thread having parallel flanks avoid a seizing up of the thread during cutting.

What is claimed is:

1. A prosthetic acetabulum for cementless fixation in a pelvis, said acetabulum having a hemispherical outer shell of biocompatible material; and a constant-pitch self-tapping screwthread on an outer peripheral surface of said shell, said thread having a cross-sectional shape of constant thickness from a free end over one-third the cross-sectional length thereof and an increasing thickness towards said shell over the remainder thereof.

2. A prosthetic acetabulum as set forth in claim 1 wherein said thread has a cross-sectional length of from 3 millimeters to 8 millimeters, a root width of from 25% to 70% of said length and a crest width at said free end of from 10% to 40% of said length.

3. A prosthetic acetabulum as set forth in claim 1 wherein said screwthread has a pitch of 6.5 millimeters.

4. A prosthetic acetabulum as set forth in claim 1 wherein said shell is made of one of titanium and a titanium alloy.

5. A prosthetic acetabulum as set forth in claim 1 wherein said screwthread is of decreasing length from an equatorial side towards a pole of said shell.

6. A one-piece metal hemispherical shell for an acetabulum, said shell having a constant-pitch self-tapping screwthread on an outer peripheral surface, said thread having a cross-sectional shape of constant thickness from a free end over a portion of the cross-sectional length thereof and an increasing thickness towards said surface over the remainder thereof.

7. A prosthetic acetabulum as set forth in claim 6 wherein said thread has a cross-sectional length of from 3 millimeters to 8 millimeters, a root width of from 25% to 70% of said length and a crest width at said free end of from 10% to 40% of said length.

8. A prosthetic acetabulum as set forth in claim 7 wherein said portion of constant thickness extends over one-third of said cross-sectional length.

9. A prosthetic acetabulum as set forth in claim 8 wherein said screwthread has a pitch of 6.5 millimeters.

10. A prosthetic acetabulum as set forth in claim 9 wherein said screwthread is of decreasing length from an equatorial side towards a pole of said shell.

* * * * *